000
United States Patent [19]

Miller et al.

[11] Patent Number: 5,549,626
[45] Date of Patent: Aug. 27, 1996

[54] VENA CAVAL FILTER

[75] Inventors: Theodore T. Miller, Larchmont; Bernard Ghelman, Cliffside Park, both of N.Y.

[73] Assignee: New York Society For The Ruptured And Crippled Maintaining The Hospital For Special Surgery, New York, N.Y.

[21] Appl. No.: 362,835

[22] Filed: Dec. 23, 1994

[51] Int. Cl.$^6$ ............................................. A61M 29/00
[52] U.S. Cl. ........................ 606/200; 606/191; 606/194; 606/195; 606/198
[58] Field of Search ............................ 606/200, 191, 606/195, 194, 198

[56] References Cited

U.S. PATENT DOCUMENTS

| | | | |
|---|---|---|---|
| 1,931,740 | 10/1933 | Ryan | 128/309 |
| 3,472,230 | 10/1969 | Fogarty | 128/328 |
| 3,908,661 | 9/1975 | Kramer | 128/305 |
| 4,425,908 | 1/1984 | Simon | 128/1 |
| 4,564,014 | 1/1986 | Fogarty et al. | 128/344 |
| 4,573,966 | 3/1986 | Weikl et al. | 604/53 |
| 4,577,631 | 3/1986 | Kreamer | 128/334 R |
| 4,585,000 | 4/1986 | Hershenson | 128/345 |
| 4,610,662 | 9/1986 | Weikl et al. | 604/53 |
| 4,655,771 | 4/1987 | Wallsten | 623/1 |
| 4,723,549 | 2/1988 | Wholey et al. | 128/344 |
| 4,790,812 | 12/1988 | Hawkins, Jr. et al. | 604/22 |
| 4,794,928 | 1/1989 | Kletschka | 128/344 |
| 4,842,579 | 6/1989 | Shiber | 604/22 |
| 4,866,061 | 12/1989 | Fischell et al. | 128/305 |
| 4,921,484 | 5/1990 | Hillstead | 604/104 |
| 4,926,858 | 5/1990 | Gifford, III, et al. | 606/159 |
| 5,059,178 | 10/1991 | Ya | 604/101 |
| 5,059,205 | 10/1991 | El-Nounou et al. | |
| 5,092,839 | 3/1992 | Kipperman | 604/53 |
| 5,100,425 | 3/1992 | Fischell et al. | 606/159 |
| 5,102,415 | 4/1992 | Guenther et al. | 606/159 |
| 5,108,419 | 4/1992 | Reger et al. | 606/200 |
| 5,152,777 | 10/1992 | Goldberg et al. | 606/200 |
| 5,154,724 | 10/1992 | Andrews | 606/159 |
| 5,160,342 | 11/1992 | Reger et al. | 606/200 |
| 5,242,462 | 9/1993 | El-Nounou et al. | |
| 5,300,086 | 4/1994 | Gory et al. | 606/200 |
| 5,324,304 | 6/1994 | Rasmussen | 606/200 |
| 5,329,942 | 7/1994 | Gunther et al. | 128/898 |

FOREIGN PATENT DOCUMENTS

0408245A1  1/1991  European Pat. Off. .

*Primary Examiner*—Michael Powell Buiz
*Assistant Examiner*—Kevin Truong
*Attorney, Agent, or Firm*—Darby & Darby, P.C.

[57] ABSTRACT

A co-axial filtering device for removing particles from arteries and veins comprises an outer catheter that can be inserted into a blood vessel and an inner catheter with a filter at its distal end. The filter is a radially expandable receptacle made of an elastic mesh structure of spring wires or plastic monofilaments. The filter expands into engagement with the walls of the blood vessel when it is pushed from the distal end of the outer catheter. A syringe is attached to the proximal end of the inner catheter and particles entrapped within the filter are aspirated through the inner catheter into the syringe. When filtering is no longer necessary, the filter can easily be removed by pulling the elastic material through the outer catheter.

3 Claims, 2 Drawing Sheets

VENA CAVAL FILTER

FIELD OF THE INVENTION

This invention relates generally to a device for filtering blood in a blood vessel, and more particularly, to a radially-expandable filtering device for temporary use in the vena cava, for example during orthopedic surgery and after long bone fractures.

BACKGROUND OF THE INVENTION

During joint replacement surgery such as total hip arthroplasty, emboli in the form of marrow fat, medullary bony debris and cement are released into the patient's bloodstream. These emboli may be released into the inferior vena cava (IVC) in large quantities during the relocation of the prosthetic femoral head into the acetabular component, which sends a shower of embolic debris into the cardiopulmonary circulation. The emboli have detrimental effects due to both mechanical pulmonary arterial blockage and potentially cardiosuppressive activity, thus requiring the emboli to be filtered.

Conventional blood filtering devices are designed primarily to filter relatively large blood clots and to be permanently placed within the blood vessel. The majority of these filters include an anchoring device to prevent migration of the filter after placement. Once the filtering device is positioned within the blood vessel, the device is permanent.

An example of such a blood clot filtering device is disclosed in U.S. Pat. No. 4,619,246 issued Oct. 28, 1986 to Molgaard-Nielsen et al. This reference discloses a collapsible filter receptacle adapted to be introduced into a blood vessel for the purpose of entrapping thrombi and emboli in the patient's blood. The Molgaard-Nielsen device has a plurality of anchoring legs secured to the filter receptacle. The free end of each anchoring leg is bent outwardly to form a hook. When the filter receptacle is positioned within the blood vessel, each hook penetrates into the wall of the vessel to hold the filter receptacle in position, thus damaging the vessel wall. Similar examples are shown in U.S. Pat. No. 5,242,462 issued Sep. 7, 1993 to E1-Nounou et al. and more recently U.S. Pat. No. 5,324,304 issued Jun. 28, 1994 to Rasmussen.

There are several disadvantages to a permanently placed filter. First, some types, if not correctly seated in the IVC, have a markedly decreased filtering ability, thus necessitating placement of a second filter. Second, the filter may accumulate so much clot as to occlude the entire vena cava, a circumstance which occurs in up to 19% of cases. Third, the rate of rupture of the IVC may be as high as 15% due to erosion of the vessel wall by the anchoring hooks of the filter. Fourth, if removal becomes necessary, it almost always must be done surgically; moreover, removal may greatly damage the vessel because over time the filter's struts become endothelialized by the interior wall of the vena cava. Fifth, a patient with a permanent filter must take anticoagulant medication for life. These disadvantages are regrettable since the placement of the filter in the vein is usually only necessary for a limited time, corresponding to the period during which there is a real risk of embolism.

A technique has been developed for temporarily placing a removable vena caval filter so that it can be withdrawn at a later time. For this, a catheter remains inserted in the vein after the filter is deployed and projects from the body at the introduction site. Unlike the prior art, this filter is capable of being flushed while positioned within the blood vessel. Because the catheter projects from the skin, it constitutes a potential source of infection.

Another technique is disclosed in U.S. Pat. No. 5,300,086 issued Apr. 5, 1994 to Gory et al. In the Gory reference, the catheter is cut outside the jugular vein, crimped to seal the proximal end and sutured just below the surface of the skin. This technique significantly reduces the risk of infection. Unfortunately, the catheter, which is relatively rigid is uncomfortable for the patient. Moreover, as with the prior art, the filter is incapable of being flushed while positioned within the blood vessel.

Another technique is disclosed in U.S. Pat. No. 5,102,415 issued Apr. 7, 1992 to Guenther et al. This reference discloses a triple catheter having a receptacle at the distal end of an intermediate catheter and a suction device at the proximal end for assisting in the removal of debris during placement of the receptacle within the blood vessel. However, the receptacle is covered with an elastic coating or membrane and thus is incapable of filtering blood in the conventional sense. Thus, the receptacle is not a filter for emboli but only a receptacle for relatively large blood clots. Furthermore, the Guenther reference requires the use of an inflatable balloon attached to the distal end of the inner catheter, which forces the clot into the receptacle. The intermediate and inner catheters must then be completely removed from the outer catheter to remove the blood clot. The receptacle of the Guenther reference does not filter the blood and must be completely removed from the patient's body to remove the blood clot.

SUMMARY OF THE INVENTION

Accordingly, it is an object of the present invention to provide a temporary vena caval filter for filtering emboli and thrombi.

Another object of the present invention is to provide an improved vena caval filter capable of being flushed while positioned within the blood vessel.

Still another object of the present invention is to provide a vena caval filtering device which does not become endothelialized and thus attached to the interior vena cava wall.

A still further object of the invention is to provide a vena caval filter which requires no hooks or the like that may tend to injure the vessel wall.

Yet another object is to provide a vena caval filter which is automatically seated correctly after it has been deployed.

In carrying out the above and other objects of the present invention, there is provided a filtering device preferably comprising inner and outer catheters each having proximal and distal ends, and a self-expanding filter attached at the distal end of the inner catheter. The filter is made of a mesh-like material through which blood can flow when it is deployed and which can be collapsed by pressure so that it can be pulled through the outer catheter when the filter is no longer needed.

DETAILED DESCRIPTION OF THE PREFERRED EMBODIMENT

Figure 1:
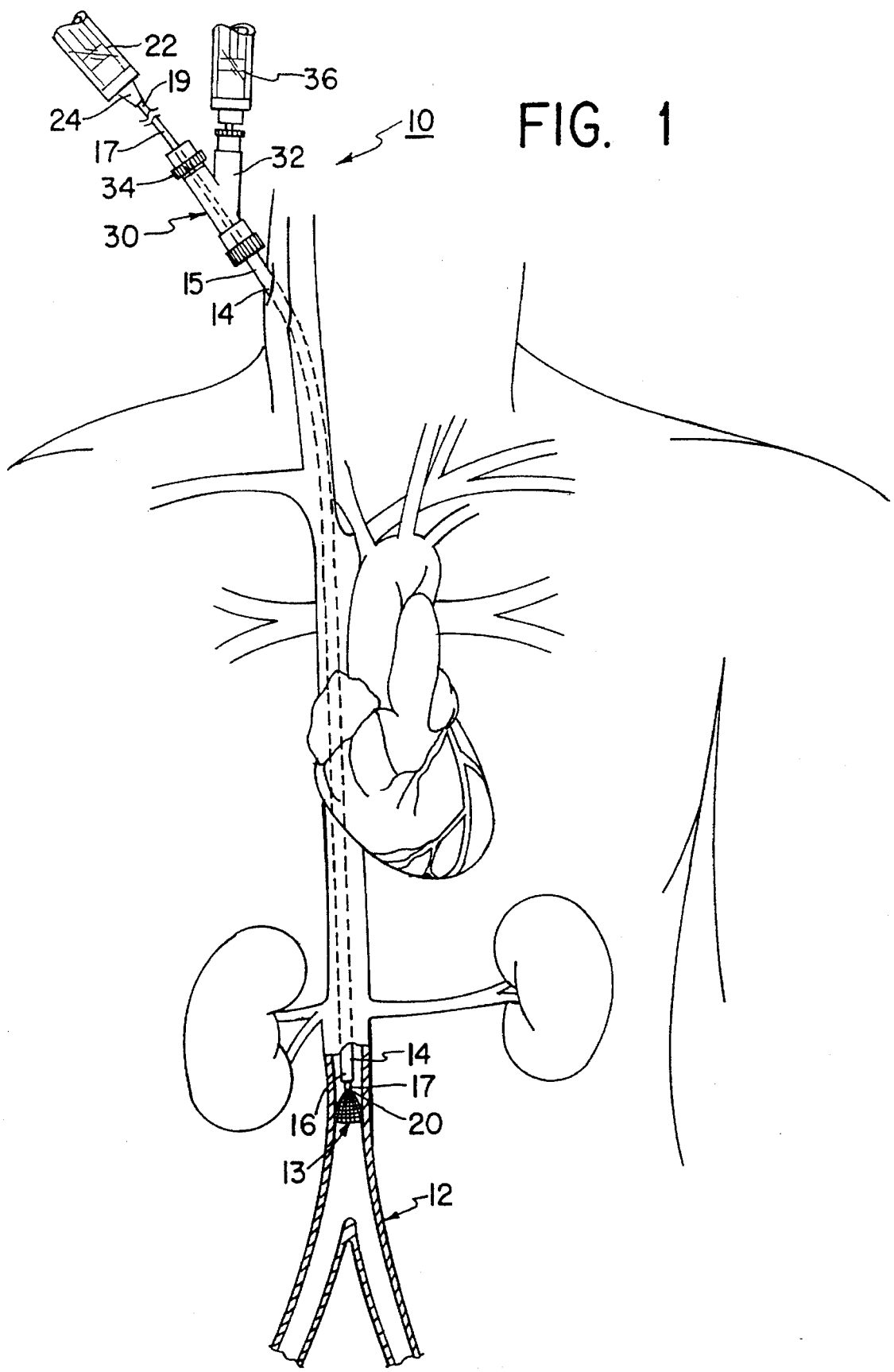
FIG. 1 is a diagrammatic view of a human body illustrating use of a vena caval filter device in accordance with the preferred embodiment of the invention.

Referring to the drawings, a preferred venal caval filter device 10 is shown in accordance with the present invention in its deployed condition wherein emboli and/or thrombi 11 (FIG. 4) are filtered from the inferior venal caval 12 using a filter 13. The filter device 10 comprises a sheath or outer catheter 14 having proximal and distal ends 15 and 16, respectively, and a coaxial inner catheter 17 which is slidable axially within a through lumen 18 of the outer catheter 14. The inner catheter 17, having proximal and distal ends 19 and 20, respectively, includes a through lumen 21 and is connected at its proximal end 19 to a suction device, preferably a syringe 22, for reasons explained below.

The filter 13 comprises a mesh-like, collapsible basket connected to the distal end 20 of the inner catheter 17 in such a way that when it is deployed (opened), the patient's blood can flow past the open filter 13 to the patient's heart (see arrow 29). After deployment, the material 11 to be filtered is aspirated through the lumen 21 of the inner catheter 17 by means of the syringe 22, which is connected to a port 24 at the proximal end 19 of the inner catheter 17.

The construction of the filter 13 is not critical and various different constructions may be used in accordance with the invention. What is necessary is that the filter be self-expanding so that when it is released from the outer catheter 14, it expands into contact with the vena cava and, of course, that it be made of a material which when expanded will block the particles of concern. The filter must also be capable of being compressed by contact with the outer catheter so that it can be withdrawn after the need for filtering no longer exists.

Materials which are suitable for use as a filter in accordance with this invention have been proposed for use as self-expanding stents. One such construction is shown in U.S. Pat. No. 4,655,771 which is incorporated herein by reference. The stent disclosed in that patent is a radially and axially flexible, elastic tubular body made of a multiplicity of thread elements defining a radially self-expanding helix. The thread elements may be metallic or plastic as described in the patent. When radial pressure is applied to such a self-expanding helix, the diameter is decreased which, in the case of the invention, means that the diameter of the filter can be decreased sufficiently so that it will fit within the outer catheter 14 when compressed.

The proximal end 15 of the outer catheter 14 is connected to a hub 30 which includes a side port 32 and a locking diaphram 34 through which the inner catheter 17 extends. This type of hub is conventional. The proximal end of inner catheter 17 may be attached to a syringe 22 by a luer lock (not numbered) so that a negative pressure can be applied to catheter 17 as described below. When locking diaphram 34 is loosened, the inner catheter 17 can be moved axially relative to the outer catheter 14. When diaphram 34 is locked, the inner catheter 17 is held in position within a fluid tight seal. The side port 32 can be connected to a syringe 36 containing a hepranized saline solution which can be forced under pressure through the outer catheter 14 after the filter 13 has been expanded. Alternatively, a pressurized IV bag may be connected to side port 32 to provide a continuous flow of hepranized saline solution between the catheters. This prevents clots from accumulating in the space between the two catheters 17 and 14.

Figure 2:
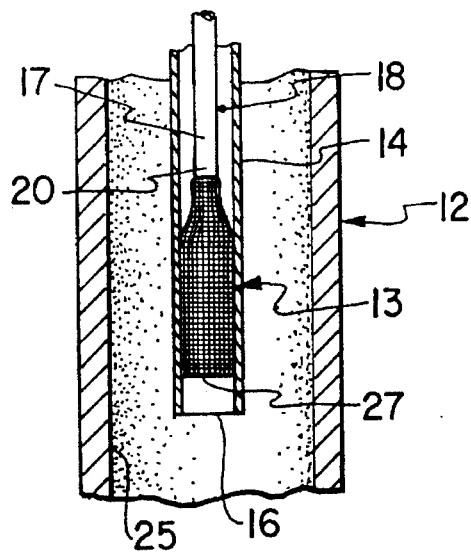
FIG. 2 is an enlarged view, partially in section, of the filter device in its retracted state.

Preferably, the filter 13 and the inner catheter 17 are loaded into the outer catheter 14 during manufacture so that the entire assembly can be positioned in the patient's blood vessel. Referring to FIGS. 1 and 2, to position the filter 13 properly within the blood vessel 12, the distal end 16 of the outer catheter 14 is inserted within the right internal jugular vein of the patient preferably using a Seldinger needle and guidewire as is well known in the art. The outer catheter 14 may include a suitable marker (not shown) at its distal end 16 to enable its position to be determined fluoroscopically so that the operator knows when the distal end 16 of catheter 14 has been advanced to the infrarenal portion of the inferior vena cava 12.

Figure 3:
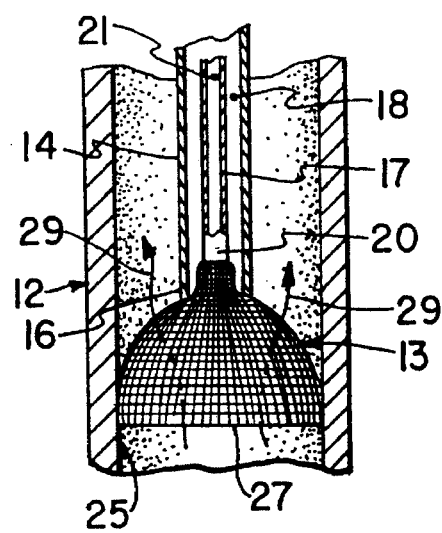
FIG. 3 is a view, partially in section, of the filter device in its expanded state.
Figure 4:
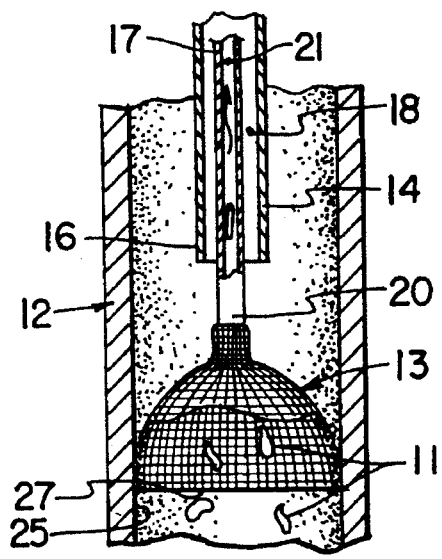
FIG. 4 is a view, partially in section, of the filter device in its expanded state showing particles being aspirated through the inner catheter into the suction device.

When the device is properly positioned, as determined fluoroscopically, the diaphram 34 is released and the inner catheter 17 advanced. As the inner catheter 17 is advanced, the filter 13 starts to exit from the distal end of the outer catheter 14, causing the filter to deploy automatically as the retaining pressure of the outer catheter is removed. When the filter is fully deployed as shown in FIGS. 3 and 4, the distal portion 27 of the filter expands into light contact with the inner surface 25 of the Vena Cava 12. This self-expanding action causes the filter to be seated correctly and retains the filter in position within the blood vessel without resort to hooks or the like which might tend to injure the vessel. Once expanded, particles 11 in the blood which flows through the filter 13 will be entrapped by the filter.

Although, in the preferred embodiment, the physician will receive the device with the inner catheter 17 and filter 13 loaded within the outer catheter 14, it is possible to provide the catheters as separate components in which case the inner catheter 17 and filter 13 would be threaded through the outer catheter 14 after the outer catheter has been positioned within the patient's blood vessel.

The filter may be deployed by pushing the inner catheter 17 so as to expel the filter from the stationary outer catheter 14 or it may be deployed by pulling the outer catheter 14 while holding the inner catheter 17 stationary. In either case, once the filter braid is free of the constraint of the outer catheter 14, it will expand into a funnel-like shape, expansion of the proximal portion of the filter being prevented by its attachment to the distal end of the inner catheter 17. In this condition, the filter 13 will prevent the undesired emboli and thrombi from passing into the aorta.

If the filter is made by the braiding process described in U.S. Pat. No. 4,655,771, particularly using metal filaments, the distal end of the filter may be enclosed in a protective rim to prevent injury to the walls of the blood vessel, and reduce the possibility of snagging as the filter is moved relative to the outer catheter 14.

Referring to FIG. 4, as the filter 13 collects emboli and thrombi 11, the syringe 22 may be used to provide a suction force that aspirates the particles 11 from the filter 13 through the lumen 21 of the inner catheter 17 and into the syringe 22, where they may be safely disposed.

The suction provided by the syringe 22 within the lumen 21 has a greater force than the force from the rate of blood flow. Thus, the blood is directed into the lumen 21 with sufficient force to flush the particles 11 from the mesh of the filter 13 into the lumen 21 and into the syringe 22. This process can be performed repeatedly during the surgery when the bulk of the particles 11 will be dislodged into the vena cava 12. Thus, the filter 13 may be flushed repeatedly without the need to remove the filter 13 from the blood vessel 12 since the flushing or suction force is provided by the syringe 22 located outside the patient.

The shape of the filter 13 is important. In the preferred embodiment, the funnel-like or inverted umbrella shape enables the filter 13 to be compressed by pulling on the inner catheter 17 causing the mesh-like material of the filter 13 to contact the distal end 16 of the outer catheter 14. Continued pressure causes the filter 13 to collapse or compress to the condition shown in FIG. 2. In this condition, the filter 13 can easily be removed after there is no longer a need for the filter 13.

While the embodiment of the invention shown and described is fully capable of achieving the results desired, it is to be understood that this embodiment has been shown and described for purposes of illustration only and not for purposes of limitation. Therefore, the invention is limited only by the appended claims.

We claim:

1. A filtering device for removing particles from a blood vessel, comprising:

an outer catheter having distal and proximal ends;

an inner catheter for insertion through said outer catheter, said inner catheter having distal and proximal ends and a through lumen, and being movable relative to said outer catheter;

a mesh-like collapsible basket attached to said distal end of said inner catheter, said basket being made of a radially expandable material which can be compressed by said outer catheter, whereby said basket will expand into contact with the blood vessel when said basket extends from said distal end of said outer catheter.

2. The filtering device of claim 1, further comprising clamping means arranged at said proximal end of said inner and outer catheters for locking said inner and outer catheters together to prevent an unintended axial displacement of said inner and outer catheters relative to each other.

3. A method for filtering particles from blood in a blood vessel of a patient comprising the steps of:

introducing an outer catheter into the blood vessel;

advancing said outer catheter to a desired location within the blood vessel;

guiding an inner catheter having a contracted mesh-like collapsible basket distally attached to said inner catheter to said desired location within said outer catheter, said inner catheter having a suction means proximally attached;

positioning said basket at a desired location beyond said distal end of said outer catheter whereby said basket expands radially within the blood vessel;

aspirating the particles from within said basket by applying suction to said inner catheter; and withdrawing the basket from the blood vessel by pulling it through said outer catheter.

* * * * *